(12) United States Patent
Su

(10) Patent No.: US 10,531,901 B2
(45) Date of Patent: Jan. 14, 2020

(54) SELF-ADJUSTABLE PECTUS RECONSTRUCTION SYSTEM

(71) Applicant: Sea-Quan Su, Taipei (TW)

(72) Inventor: Sea-Quan Su, Taipei (TW)

(*) Notice: Subject to any disclaimer, the term of this patent is extended or adjusted under 35 U.S.C. 154(b) by 27 days.

(21) Appl. No.: 15/641,358

(22) Filed: Jul. 5, 2017

(65) Prior Publication Data

US 2018/0303527 A1 Oct. 25, 2018

(30) Foreign Application Priority Data

Apr. 20, 2017 (TW) .............................. 106113333 A

(51) Int. Cl.
*A61B 17/80* (2006.01)

(52) U.S. Cl.
CPC ...... *A61B 17/8076* (2013.01); *A61B 17/8004* (2013.01); *A61B 17/8023* (2013.01)

(58) Field of Classification Search
CPC ............ A61B 17/8004; A61B 17/8014; A61B 17/8023; A61B 17/8076
See application file for complete search history.

(56) References Cited

U.S. PATENT DOCUMENTS

| | | | |
|---|---|---|---|
| 9,782,260 B1* | 10/2017 | Anissian | A61F 2/34 |
| 2009/0076509 A1* | 3/2009 | Bush, Jr. | A61B 17/7059 606/71 |
| 2010/0256691 A1* | 10/2010 | Park | A61B 17/8076 606/330 |
| 2017/0065358 A1* | 3/2017 | Gauneau | A61B 50/30 |

FOREIGN PATENT DOCUMENTS

| | | |
|---|---|---|
| CN | 202446232 U | 9/2012 |
| CN | 203693730 U | 7/2014 |
| CN | 105662559 A | 6/2016 |

OTHER PUBLICATIONS

TW Office Action dated Jan. 23, 2018 in corresponding Taiwan Patent Appin. No. TWI627934B granted on Jul. 1, 2018.

* cited by examiner

*Primary Examiner* — Amy R Sipp
(74) *Attorney, Agent, or Firm* — Bacon & Thomas, PLLC

(57) ABSTRACT

A self-adjustable pectus reconstruction system comprising: a pectus reconstruction bar having a first end and a first slot disposed on the first end; a first fixing unit having a first channel; and a first connector, wherein the first end of the pectus reconstruction bar is assembled on the first channel of the first fixing unit, the first connector passes through the first slot to combine the pectus reconstruction bar with the first fixing unit, and the first slot of the pectus reconstruction bar is capable of sliding back and forth around the first connector.

20 Claims, 8 Drawing Sheets

SELF-ADJUSTABLE PECTUS RECONSTRUCTION SYSTEM

CROSS REFERENCE TO RELATED APPLICATION

This application claims the benefits of the Taiwan Patent Application Serial Number 106113333, filed on Apr. 20, 2017, the subject matter of which is incorporated herein by reference.

BACKGROUND OF THE INVENTION

Field of the Invention

The present invention provides a self-adjustable pectus reconstruction system having a self-adjustable structure that can be self-stretching when a patient breathes and providing an expanded space to avoid growth limitation.

Description of Related Art

Pectus excavatum is a congenital disease because of an abnormal hyperplasia of cartilago costalis on the both sides of sternum and leads to a concave sternum; when the symptom is severe, it will oppress the heart and lungs leading to abnormal conditions such as dyspnea, chest pain, cardiopulmonary dysfunction and the like. Commonly, cardiopulmonary dysfunction is less found in childhood, whereas it becomes severe in adolescence.

A traditional treatment is to remove the deformation of cartilago costalis so as to regenerate cartilago costalis and elevate the concave sternum simultaneously. Nowadays, the traditional treatment is replaced by a minimally invasive surgery, a tailor-made metal plate is placed behind the sternum in order to push out the concave sternum and cartilage costalis without resection surgery, and the metal plate should be retained in the body for at least 2 to 4 years before removal.

However, most of the orthopedic internal fixation implants cannot automatically adjust the length, size, and position to conform to human growth or the respiratory changes without affecting clinical functions; therefore, it causes discomfort after implantation and even needs re-implantation to conform to patient's body growth. Accordingly, it is necessary to develop a bone orthopedic appliance which is self-adjustable to conform to patient's growth or respiratory changes.

SUMMARY OF THE INVENTION

The present invention provides a self-adjustable pectus reconstruction system having a self-adjustable structure that can be self-stretching and reduce the patient's pain and foreign body sensation when the patient breathes. In addition, since many patients receiving pectus excavatum correction surgeries are children and young people, the present invention having self-adjustable structure can provide an expanded space to avoid growth limitation. Meanwhile, the fixing unit of the present invention can be arc-shaped for conforming to ergonomics to avoid foreign body sensation and the risk of patient's skin extrusion.

The present invention provides a self-adjustable pectus reconstruction system, comprising: a pectus reconstruction bar having a first end and a first slot disposed on the first end; a first fixing unit having a first channel; and a first connector, wherein the first end of the pectus reconstruction bar is assembled on the first channel of the first fixing unit, the first connector passes through the first slot to combine the pectus reconstruction bar with the first fixing unit, and the first slot is capable of sliding back and forth around the first connector. Wherein the first fixing unit further comprises a first through-hole, and the system is fixed to a tissue by the first through-hole of the first fixing unit. Wherein the system further comprises a second fixing unit and a second connector, and the second fixing unit is combined with the pectus reconstruction bar by the second connector. Wherein an extended direction of the first slot is parallel to a longitudinal direction of the pectus reconstruction bar. Wherein the pectus reconstruction bar comprises an arc-shaped structure to fit patient's shape of sternum.

The present invention provides a further self-adjustable pectus reconstruction system, further comprising: a second end and a second slot disposed on the second end, the second fixing unit having a second channel, wherein the second end of the pectus reconstruction bar is assembled on the second channel of the second fixing unit, the second connector passes through the second slot to combine the pectus reconstruction bar with the second fixing unit, and the second slot is capable of sliding back and forth around the second connector. Wherein the second fixing unit further comprises a second through-hole, and the system is fixed to a tissue by the second through-hole of the second fixing unit. Wherein an extended direction of the second slot is parallel to a longitudinal direction of the pectus reconstruction bar.

Since the pectus reconstruction system needs to be placed in patients' body for a long period of time, the present invention has taken patients' needs into consideration. The self-adjustable pectus reconstruction system provided by the present invention is characterized by having a self-adjustable structure that can adjust its structure when the patient is breathing, the slot can slide back and forth around the connector according to the movement of sternum, and adjust its length automatically so as to reduce pain and foreign body sensation. In addition, the self-adjustable structure provides the patient with an expanded space to avoid growth limitation at the same time.

In a further embodiment of the present invention, the first and second fixing units of the self-adjustable pectus reconstruction system may optionally have an arc-shaped structure for fitting patient's sternum to avoid foreign body sensation. In the self-adjustable pectus reconstruction system, the first fixing unit and second fixing unit are hermetic to prevent human tissue from migrating into the first fixing unit and second fixing unit causing a system failure or difficulty of removing the system afterwards.

In addition, the present invention further provides a method for reconstructing pectus excavatum by using the aforementioned self-adjustable pectus reconstruction system. The method of the present invention may comprise the following steps: providing the aforementioned self-adjustable pectus reconstruction system; passing the pectus reconstruction bar behind patient's deformed sternum; rotating the pectus reconstruction bar whereby the deformed sternum is raised into a desired position; and fixing the pectus reconstruction bar onto the patient's bone through the fixing unit.

Other objects, advantages, and novel features of the invention will become more apparent from the following detailed description when taken in conjunction with the accompanying drawings.

DETAILED DESCRIPTION OF THE PREFERRED EMBODIMENT

Although the present invention has been explained in relation to its preferred embodiment, it is to be understood that many other possible modifications and variations can be made without departing from the spirit and scope of the invention as hereinafter claimed.

In addition, ordinal numbers such as "first", "second" and the like used in the specification and claims for modifying elements of the claims do not mean and represent the claimed elements have any antecedent ordinal number, nor do it represent the order (or order of production) between a claimed element and another claimed element. The ordinal numbers are only used to clearly distinguish certain claimed elements having the same name.

Embodiment 1

Figure 1:
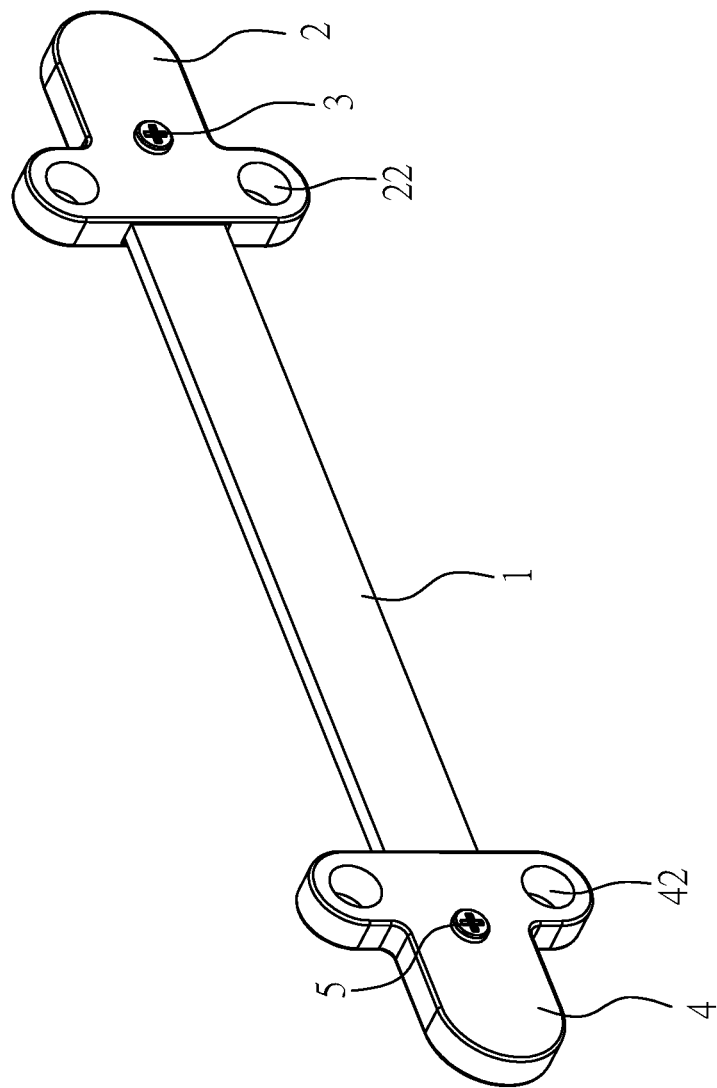
FIG. 1 is a system diagram according to Embodiment 1 of the present invention
Figure 2:
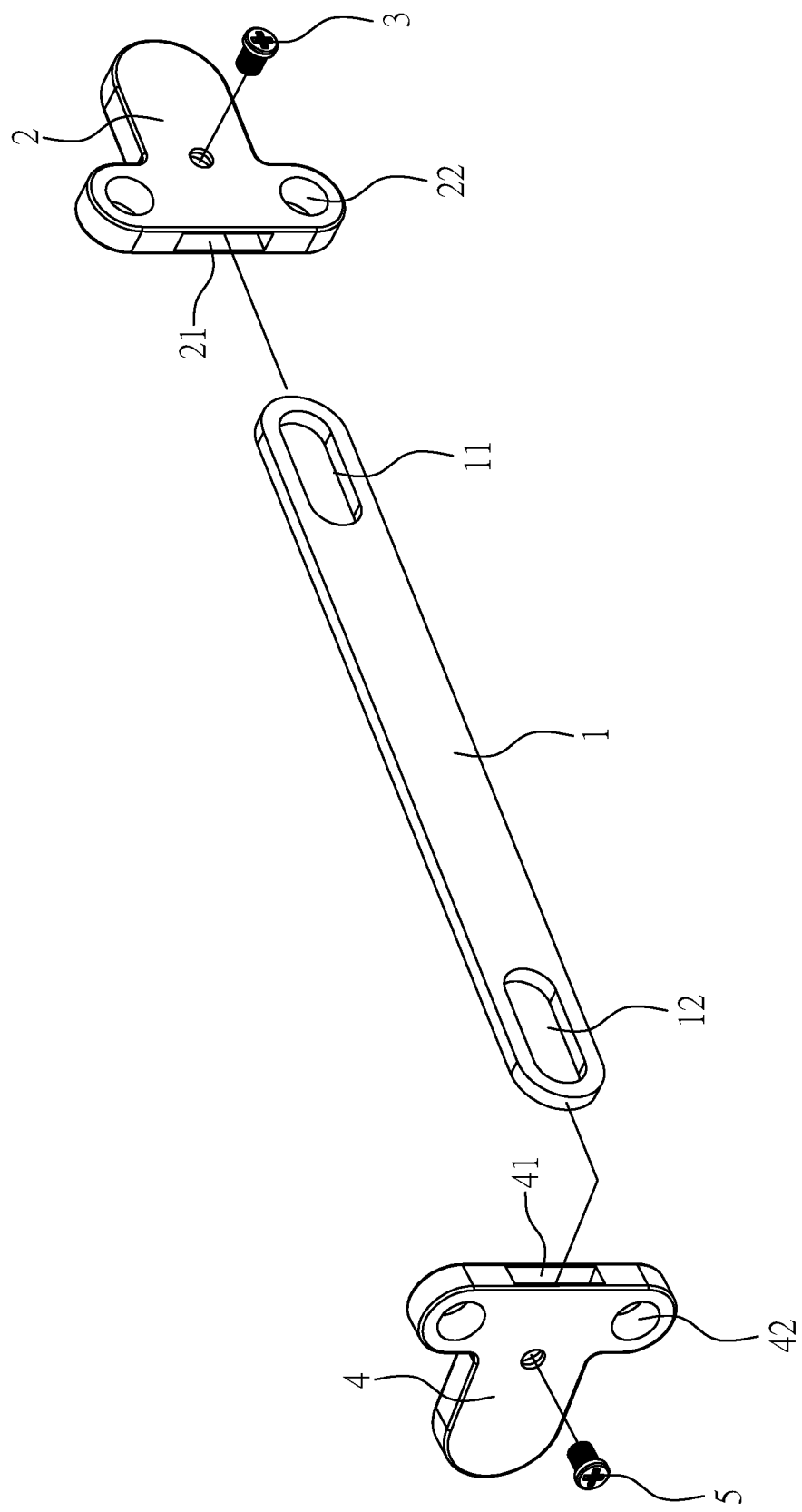
FIG. 2 is an assembly diagram according to Embodiment 1 of the present invention
Figure 3:
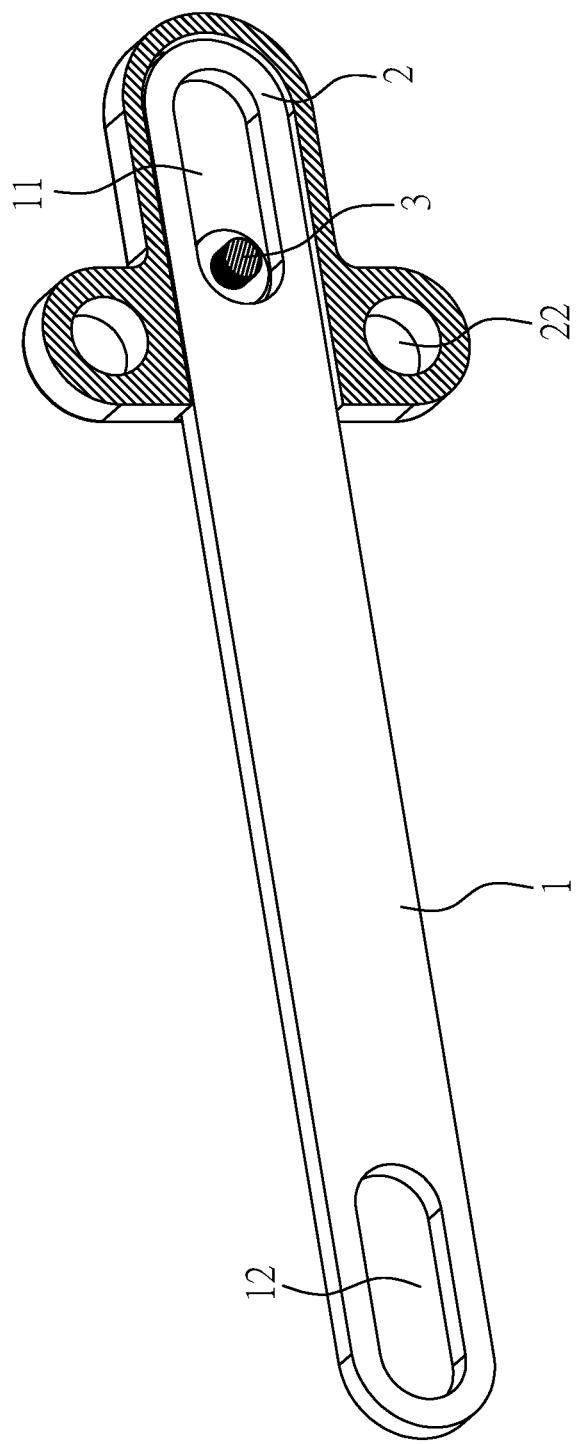
FIG. 3 is a cross sectional view of one end according to Embodiment 1 of the present invention
Figure 7:
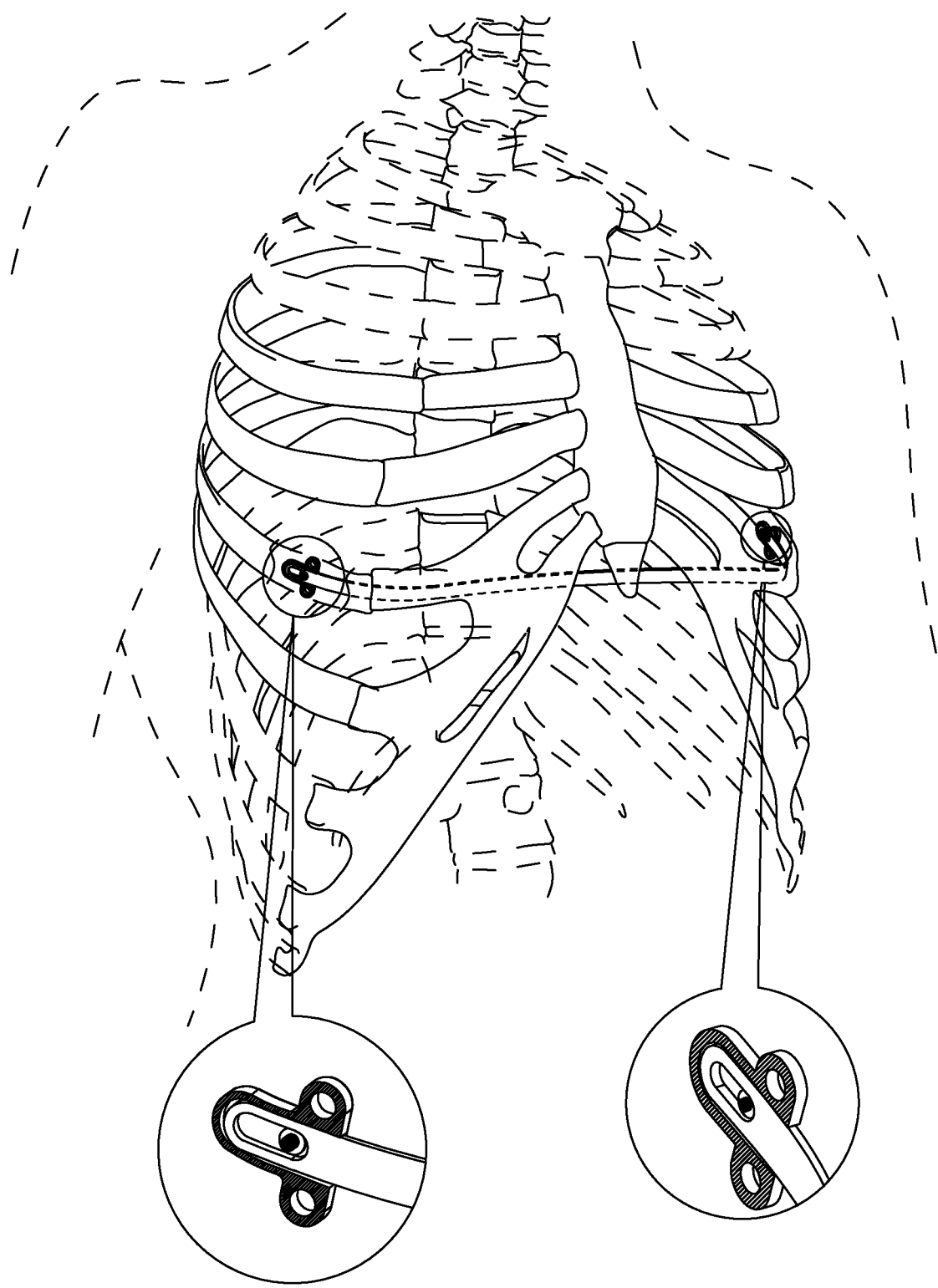
FIG. 7 is a schematic diagram showing correction of pectus excavatum according to Embodiment 1.
Figure 8:
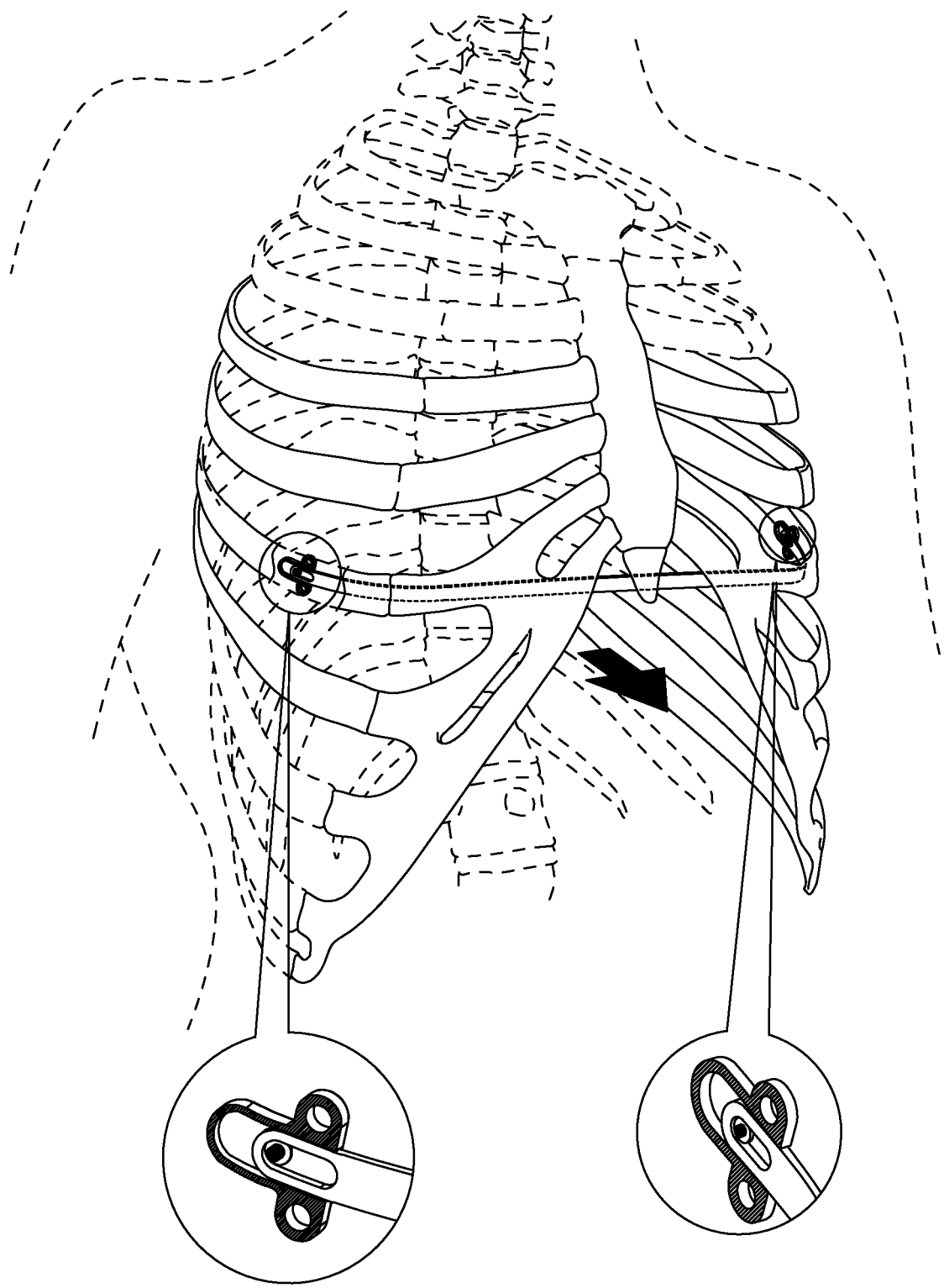
FIG. 8 is a schematic diagram showing correction of pectus excavatum according to Embodiment 1.

FIG. 1 is a system diagram of the present embodiment, FIG. 2 is an assembly diagram of FIG. 1, FIG. 3 is a cross sectional view of a first end, FIG. 7 is a schematic diagram showing correction of pectus excavatum, and FIG. 8 is another schematic diagram showing correction of pectus excavatum.

A self-adjustable pectus reconstruction system of the present embodiment comprises: a pectus reconstruction bar 1 having a first end and a first slot 11 disposed on the first end; a first fixing unit 2 having a first channel 21; and a first connector 3, wherein the first end of the pectus reconstruction bar 1 is assembled on the first channel 21 of the first fixing unit 2, the first connector 3 passes through the first slot 11 to combine the pectus reconstruction bar 1 with the first fixing unit 2, and the first slot 11 of the pectus reconstruction bar 1 is capable of sliding back and forth around the first connector 3. Wherein the first fixing unit 2 further comprises a first through-hole 22, and the system is fixed to a tissue by the first through-hole 22 of the fixing unit 2. Wherein an extended direction of the first slot 11 is parallel to a longitudinal direction of the pectus reconstruction bar 1.

The self adjustable pectus reconstruction system of the present embodiment further comprises a second fixing unit 4 and a second connector 5. The pectus reconstruction bar further comprises a second end and a second slot 12 disposed on the second end, the second fixing unit 4 has a second channel 41, the second end of the pectus reconstruction bar 1 is assembled on the second channel 41 of the second fixing unit 4, the second connector 5 passes through the second slot 12 to combine the pectus reconstruction bar 1 with the second fixing unit 4, and the second slot 12 of the pectus reconstruction bar 1 is capable of sliding back and forth around the second connector 5. Furthermore, an extended direction of the second slot 12 is parallel to a longitudinal direction of the pectus reconstruction bar 1. Wherein the second fixing unit 4 further comprises a second through-hole 42, and the system is fixed to a tissue by the second through-hole 42 of the second fixing unit 4.

Referring to FIG. 7, it shows a cross sectional view of the first end and the second end of the present embodiment fixed to a human tissue, and the sternum is in its original position when the human body is in an expiratory state. Referring to FIG. 8, it shows a cross sectional view of the first end and the second end of the present embodiment fixed to a human tissue, and the sternum is raised when the human body is in an inspiratory state. Since the present invention has self-adjustable structure, it can adjust its structure when the patient is breathing. The slot of the pectus reconstruction bar can slide back and forth around the connector according to the movement of sternum, and adjust its length automatically so as to reduce pain and foreign body sensation. In addition, the self-adjustable structure provides the patient with an expanded space to avoid growth limitation at the same time. Herein, the first fixing unit and the second fixing unit in cross sectional views are shown in FIG. 7 and FIG. 8 to clearly show the relative positions between the pectus reconstruction bar and the first and second fixing units. In an actual situation, the first fixing unit and the second fixing unit used in the patient are not those shown in FIG. 7 and FIG. 8, but are those shown in FIG. 1 and FIG. 2.

The material of the pectus reconstruction bar may be selected from materials known in the art such as stainless steel, titanium alloy and the like; and the slot may be bar-shaped such as elliptical- or rectangular-shaped. The material of the fixing unit can be the same as or different from the material of pectus reconstruction bar, and may be selected from materials known in the art such as stainless steel, titanium alloy and the like. The connector can be any fixing element. The first fixing unit and the second fixing unit are hermetic to prevent human tissue from migrating into the first and second fixing unit causing a system failure or difficulty of removing the system afterwards.

Embodiment 2

Figure 4:
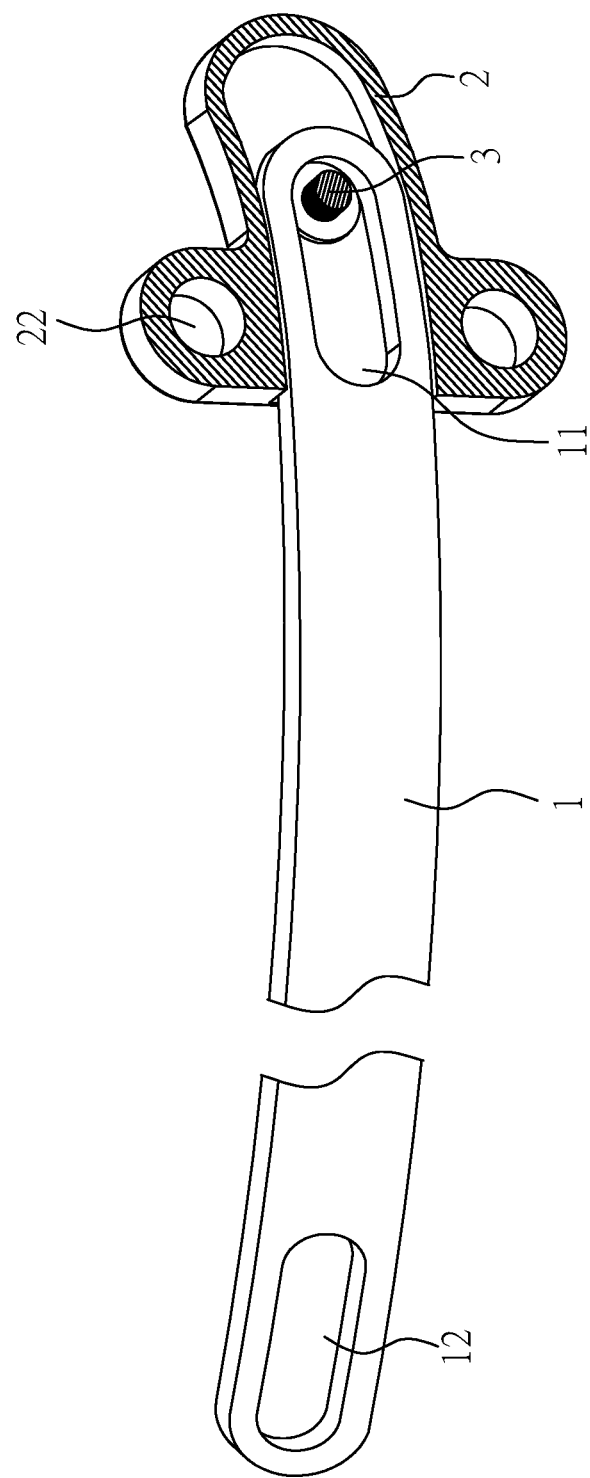
FIG. 4 is a cross sectional view of one end according to Embodiment 2 of the present invention

FIG. 4 is a cross sectional view of one end according to the present embodiment; wherein the self-adjustable pectus reconstruction system of the present embodiment is similar to that of Embodiment 1 or 2 except for the following differences.

Referring to FIG. 4, in the present embodiment, the first fixing unit 2 and/or second fixing unit (not shown) may have an arc-shaped structure if necessary. In addition, the pectus reconstruction bar 1 comprises an arc-shaped structure to fit patient's shape of sternum. When the first fixing unit 2, the second fixing unit and/or pectus reconstruction bar 1 have an arc-shaped structure, it can fit patient's shape of sternum more to avoid foreign body sensation and the risk of patient's skin extrusion.

Embodiment 3

Figure 5:
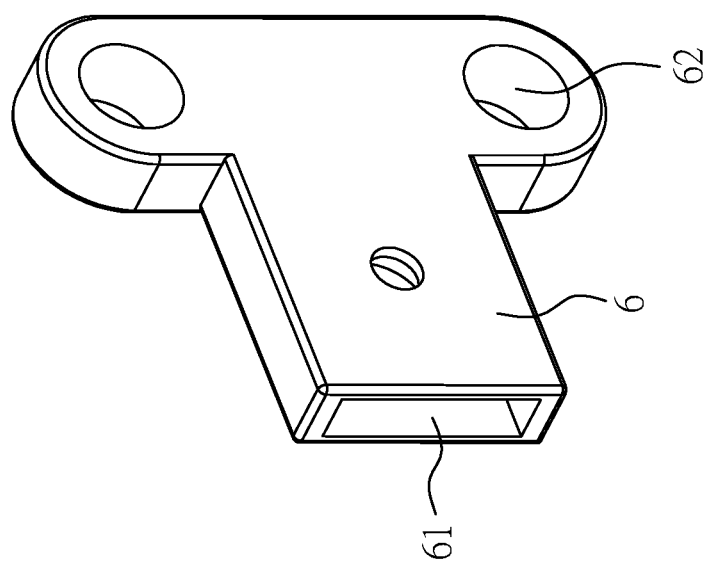
FIG. 5 is a schematic diagram of a fixing unit according to Embodiment 3 of the present invention

FIG. 5 is a schematic diagram of a fixing unit of the present embodiment. As shown in FIG. 1 through 4, the first through-hole 22 of the first fixing unit 2 and/or the second through-hole 42 of the second fixing unit 4 can be plural according to the pectus reconstruction system in Embodiment 1 or Embodiment 2. In the present embodiment, the first fixing unit 6 has a first channel 61, and the first through-hole 62 of the first fixing unit 6 and/or the second through-hole of the second fixing unit (not shown) can be plural and disposed on both ends of the fixing unit. The amount and installation position of the through-holes of the first fixing unit 6 and/or the second fixing unit are not particularly limited, as long as they can fix the system to a tissue.

Embodiment 4

Figure 6:
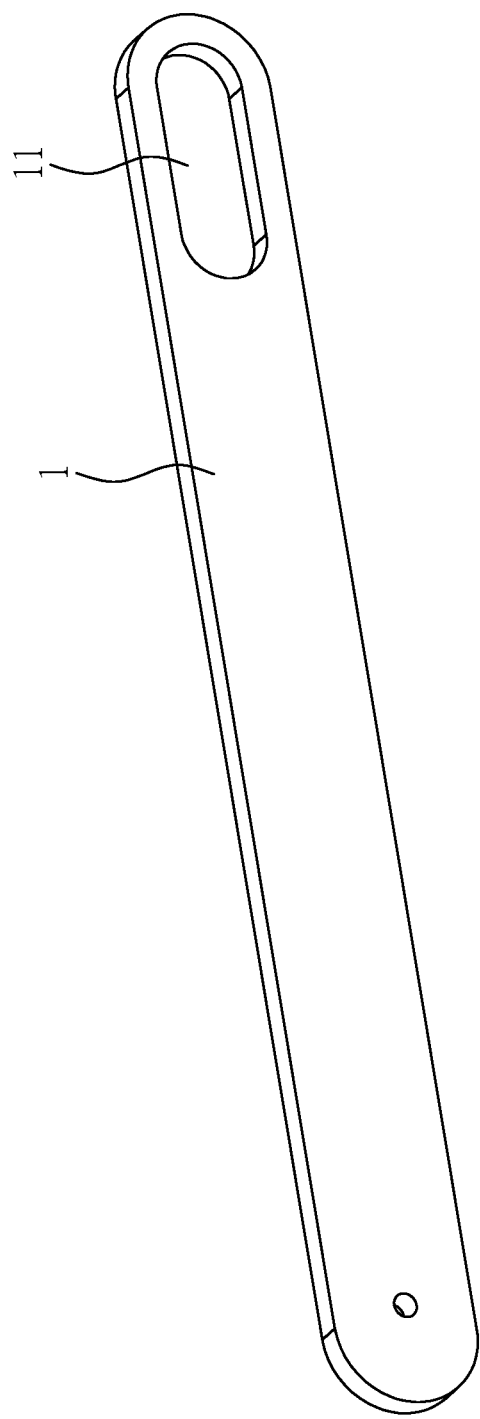
FIG. 6 is a schematic diagram of a pectus reconstruction bar according to Embodiment 4 of the present invention

FIG. 6 is a schematic diagram of the pectus reconstruction bar according to the present embodiment; wherein the self-adjustable pectus reconstruction system of the present embodiment is similar to Embodiment 1 except for the following differences.

Referring to FIG. 6, in the present embodiment, the pectus reconstruction bar 1 comprises a first end and a first slot 11 disposed on the first end, whereas there is no second slot disposed on the second end of the pectus reconstruction bar 1. Therefore, there is only one self-adjustable structure disposed on one end of the self-adjustable pectus reconstruction system of the present embodiment. Accordingly; it is an aspect of the reconstruction system that one end of the system is self-adjustable, whereas another end is not self-adjustable.

Embodiment 5

Firstly, provide a tailor-made pectus reconstruction bar of the reconstruction system according to patient's anterior chest wall curvature, make an incision of 1.5 to 2 cm long on each side of the lateral chest wall between the anterior axillary and posterior axillary lines, pass the self-adjustable pectus reconstruction bar behind patient's deformed sternum in order to push out the concave sternum and deformed cartilage costalis, rotate the pectus reconstruction bar whereby the deformed sternum is raised into a desired position, fix the bar onto patient's bone through the fixing unit, retain the pectus reconstruction system within the patient for 2-4 years depending on the patient's age and condition, and then remove the pectus reconstruction system after the shape of the sternum is fixed.

In contrast to traditional surgery, the self-adjustable pectus reconstruction system of the present invention has the following advantages: a minimally invasive technique which requires shorter operating time, smaller incision, less dissection, less sterna fracturing, less pain, quick postoperative recovery, shorter hospital stay, and retaining patient's bone elasticity of the anterior chest wall.

The self-adjustable pectus reconstruction system can be self-stretching to reduce patient's pain and foreign body sensation when the patient is breathing. It also provides an expanded space to avoid patient's body growth limitation. Meanwhile, the fixing unit can be arc-shaped for conforming to ergonomics to avoid foreign body sensation and the risk of skin extrusion.

Said embodiments shall to be construed as merely illustrative and not in any way limit the remainder of the disclosure.

What is claimed is:

1. A self-adjustable pectus reconstruction system, comprising:
    a pectus reconstruction bar having a first end and a first slot disposed in the first end;
    a first unitary fixing unit having a first channel; and
    a first connector,
    wherein the first slot is elongated in a lengthwise direction of the pectus reconstruction bar,
    wherein the first end of the pectus reconstruction bar is assembled in the first channel of the first unitary fixing unit, the first connector passes through the first slot to combine the pectus reconstruction bar with the first unitary fixing unit, and the first slot of the pectus reconstruction bar is capable of sliding back and forth around the first connector, and
    wherein the first unitary fixing unit extends in the lengthwise direction so that the first slot is enclosed within the first unitary fixing unit without being exposed to tissue, thereby preventing ingrowth of the tissue into the first slot.

2. The system as claimed in claim 1, wherein the first unitary fixing unit further comprises a first through-hole, and the system is fixed to a bone via the first through-hole of the first unitary fixing unit.

3. The system as claimed in claim 1, further comprising a second unitary fixing unit and a second connector, wherein the second unitary fixing unit is combined with the pectus reconstruction bar by the second connector.

4. The system as claimed in claim 3, wherein the pectus reconstruction bar further comprises:
    a second end and a second slot disposed in the second end; and
    the second unitary fixing unit having a second channel;
    wherein the second slot is elongated in the lengthwise direction of the pectus reconstruction bar,
    wherein the second end of the pectus reconstruction bar is assembled in the second channel of the second unitary fixing unit, the second connector passes through the second slot to combine the pectus reconstruction bar with the second unitary fixing unit, and the second slot of the pectus reconstruction bar is capable of sliding back and forth around the second connector, and
    the second unitary fixing unit extends in the lengthwise direction so that the second slot is enclosed within the second unitary fixing unit without being exposed to tissue, thereby preventing ingrowth of the tissue into the second slot.

5. The system as claimed in claim 4, wherein an extended direction of the second slot is parallel to a longitudinal direction of the pectus reconstruction bar.

6. The system as claimed in claim 3, wherein the second unitary fixing unit further comprises a second through-hole, and the system is fixed to a bone via the second through-hole of the second unitary fixing unit.

7. The system as claimed in claim 3, wherein the second unitary fixing unit has an arc-shaped structure and the second unitary fixing unit hermetically encloses a second end of the pectus reconstruction bar.

8. The system as claimed in claim 1, wherein an extended direction of the first slot is parallel to a longitudinal direction of the pectus reconstruction bar.

9. The system as claimed in claim 1, wherein the pectus reconstruction bar comprises an arc-shaped structure.

10. The system as claimed in claim 1, wherein the first unitary fixing unit has an arc-shaped structure and the first unitary fixing unit hermetically encloses the first end of the pectus reconstruction bar.

11. A method for reconstructing pectus excavatum comprising:
    providing the self-adjustable pectus reconstruction system as claimed in claim 1, comprising the steps of:
        passing the pectus reconstruction bar behind patient's deformed sternum;

rotating the pectus reconstruction bar whereby the deformed sternum is raised into a desired position; and fixing the pectus reconstruction bar onto a bone via the first unitary fixing unit.

12. The method as claimed in claim 11, wherein the first unitary fixing unit further comprises a first through-hole, and the system is fixed to the bone via the first through-hole of the first unitary fixing unit.

13. The method as claimed in claim 11, wherein the self-adjustable pectus reconstruction system further comprises a second unitary fixing unit and a second connector, wherein the second unitary fixing unit is combined with the pectus reconstruction bar by the second connector.

14. The method as claimed in claim 13, wherein the pectus reconstruction bar further comprises:
a second end and a second slot disposed in the second end; and
the second unitary fixing unit having a second channel;
wherein the second slot is elongated in the lengthwise direction of the pectus reconstruction bar,
wherein the second end of the pectus reconstruction bar is assembled in the second channel of the second unitary fixing unit, the second connector passes through the second slot to combine the pectus reconstruction bar with the second unitary fixing unit, and the second slot of the pectus reconstruction bar is capable of sliding back and forth around the second connector, and the second unitary fixing unit extends in the lengthwise direction so that the second slot is enclosed within the second unitary fixing unit without being exposed to tissue, thereby preventing ingrowth of the tissue into the second slot.

15. The method as claimed in claim 14, wherein an extended direction of the second slot is parallel to a longitudinal direction of the pectus reconstruction bar.

16. The method as claimed in claim 13, wherein the second unitary fixing unit further comprises a second through-hole, and the system is fixed to the bone via the second through-hole of the second unitary fixing unit.

17. The method as claimed in claim 13, wherein the second unitary fixing unit has an arc-shaped structure and the second unitary fixing unit hermetically encloses a second end of the pectus reconstruction bar.

18. The method as claimed in claim 11, wherein an extended direction of the first slot is parallel to a longitudinal direction of the pectus reconstruction bar.

19. The method as claimed in claim 11, wherein the pectus reconstruction bar comprises an arc-shaped structure.

20. The method as claimed in claim 11, wherein the first unitary fixing unit has an arc-shaped structure and the first unitary fixing unit hermetically encloses the first end of the pectus reconstruction bar.

* * * * *